United States Patent
Pillai et al.

(10) Patent No.: US 10,071,159 B2
(45) Date of Patent: *Sep. 11, 2018

(54) ORAL CARE COMPOSITIONS

(75) Inventors: Shyamala Pillai, Piscataway, NJ (US);
Lin Fei, Kendall Park, NJ (US);
Guofeng Xu, Plainsboro, NJ (US)

(73) Assignee: Colgate-Palmolive Company, New York, NY (US)

(*) Notice: Subject to any disclaimer, the term of this patent is extended or adjusted under 35 U.S.C. 154(b) by 248 days.

This patent is subject to a terminal disclaimer.

(21) Appl. No.: 13/982,846

(22) PCT Filed: Jan. 31, 2011

(86) PCT No.: PCT/US2011/023099
§ 371 (c)(1),
(2), (4) Date: Jul. 31, 2013

(87) PCT Pub. No.: WO2012/105932
PCT Pub. Date: Aug. 9, 2012

(65) Prior Publication Data
US 2013/0315844 A1  Nov. 28, 2013

(51) Int. Cl.
| | |
|---|---|
| A61K 8/21 | (2006.01) |
| A61K 8/97 | (2017.01) |
| A61Q 11/00 | (2006.01) |
| A61K 8/23 | (2006.01) |
| A61K 36/57 | (2006.01) |
| A61K 36/575 | (2006.01) |
| A61K 47/02 | (2006.01) |
| A61K 8/35 | (2006.01) |
| A61K 8/99 | (2017.01) |
| A61Q 19/08 | (2006.01) |
| A61K 31/105 | (2006.01) |
| A61K 8/34 | (2006.01) |
| A61K 8/19 | (2006.01) |

(52) U.S. Cl.
CPC .......... *A61K 47/02* (2013.01); *A61K 8/19* (2013.01); *A61K 8/347* (2013.01); *A61K 8/35* (2013.01); *A61K 8/99* (2013.01); *A61K 31/105* (2013.01); *A61Q 11/00* (2013.01); *A61Q 19/08* (2013.01)

(58) Field of Classification Search
CPC ........ A61K 36/575; A61K 31/05; A61K 8/21; A61K 8/97; A61Q 11/00
USPC .................................................. 424/49, 58
See application file for complete search history.

(56) References Cited

U.S. PATENT DOCUMENTS

| | | | |
|---|---|---|---|
| 6,207,137 B1 * | 3/2001 | Shuch | A61K 8/355 424/49 |
| 6,500,409 B1 | 12/2002 | Scherl et al. | |
| 7,438,895 B2 | 7/2008 | Gallis | |
| 7,592,025 B2 | 9/2009 | Dodds et al. | |
| 7,744,932 B2 | 6/2010 | Faller et al. | |
| 2006/0013779 A1 | 1/2006 | Dodds et al. | |
| 2006/0110336 A1 | 5/2006 | McGill et al. | |
| 2006/0127329 A1 | 6/2006 | Xu et al. | |
| 2006/0134024 A1 | 6/2006 | Trivedi et al. | |
| 2006/0140885 A1 * | 6/2006 | Gaffar | A61K 36/575 424/58 |
| 2006/0141073 A1 | 6/2006 | Worrell et al. | |
| 2007/0041914 A1 | 2/2007 | Gaffar et al. | |
| 2007/0134171 A1 | 6/2007 | Dodds et al. | |
| 2007/0140990 A1 * | 6/2007 | Fetissova | A61K 8/21 424/50 |
| 2009/0087501 A1 | 4/2009 | Cummins | |
| 2009/0130154 A1 | 5/2009 | Gupta | |
| 2009/0186090 A1 | 7/2009 | Zaidel et al. | |
| 2009/0202452 A1 | 8/2009 | Robinson et al. | |
| 2009/0317461 A1 | 12/2009 | Bazemore et al. | |
| 2012/0128599 A1 * | 5/2012 | Schaeffer-Korbylo et al. 424/48 | |
| 2013/0129643 A1 * | 5/2013 | Mirajkar et al. ................ 424/56 | |

FOREIGN PATENT DOCUMENTS

| | | |
|---|---|---|
| CN | 101115530 | 1/2008 |
| CN | 101864349 A1 | 10/2010 |
| JP | S57-085319 | 5/1982 |
| JP | S60-075416 | 4/1985 |
| JP | H08-175945 | 7/1996 |
| JP | 2003-183141 A | 7/2003 |
| JP | 2008-115114 A | 5/2008 |
| JP | 2008-115115 A | 5/2008 |
| JP | 2007033649 | 8/2008 |
| KR | 20110001472 | 1/2011 |
| WO | 200185116 A1 | 11/2001 |
| WO | WO 0182922 | 11/2001 |
| WO | 2006071654 A1 | 7/2006 |
| WO | 2006101818 A1 | 9/2006 |
| WO | 2006101864 A1 | 9/2006 |
| WO | WO2007064519 A1 | 6/2007 |
| WO | WO2009148875 A1 | 12/2009 |

OTHER PUBLICATIONS

Database WPI, Week 201113, Thomson Scientific, 2010-P32877 XP002663063, 1 p.
International Search Report and Written Opinion of the International Searching Authority issued in International Application PCT/US2011/023099 dated Nov. 28, 2011.
Written Opinion of the International Preliminary Examining Authority issued in International Application PCT/US2011/023099 dated Jan. 29, 2013.
Greenberg et al., "Compressed mints and chewing gum containing magnolia bark extract arew effective against bacteria responsible for oral malodor," J. Agric. Food Chem., Nov. 2007, 55(23):9465-9.

* cited by examiner

*Primary Examiner* — Lezah Roberts

(57) ABSTRACT

Described herein are compositions comprising an active compound from an extract of magnolia, or a derivative thereof; and a non-surfactant electrolyte in an amount effective to stabilize the composition, and methods of making and using the same.

8 Claims, No Drawings

ORAL CARE COMPOSITIONS

BACKGROUND

Maintaining the stability of compositions containing one or more active compounds from magnolia extract is a problem encountered by product formulators. Embodiments of the present invention provide compositions which address, inter alia, this problem.

SUMMARY

In some embodiments, the present invention provides oral care compositions comprising an active compound from an extract of magnolia, and a non-surfactant electrolyte in an amount effective to stabilize the composition. In some embodiments, the non-surfactant electrolyte is present in an amount effective to enhance the solubility of the active compound from an extract of magnolia.

In other embodiments, the present invention provides a method of treating a disease or condition of the oral cavity comprising contacting an oral cavity surface of a subject in need thereof with any one of the compositions described herein.

DETAILED DESCRIPTION

As used throughout, ranges are used as shorthand for describing each and every value that is within the range. Any value within the range can be selected as the terminus of the range.

In addition, all references cited herein are hereby incorporated by reference in their entireties.

In the event of a conflict in a definition in the present disclosure and that of a cited reference, the present disclosure controls.

In some embodiments, the present invention provides a composition comprising: an antibacterial effective amount of an active compound from an extract of magnolia; a non-surfactant electrolyte in an amount effective to stabilize the composition; and an orally acceptable carrier. In some embodiments, the composition is an oral care composition. In some embodiments, the composition is a personal care composition.

The orally acceptable carrier will vary according to the form of the composition and is typically present in an amount of from about 20 to 99% by weight. A typical toothpaste composition may contain 15% glycerol and 20% water. A typical mouthwash or fluid composition may contain 94% of the sum of water, alcohol, and glycerin.

As used herein, the amount of non-surfactant electrolyte effective or sufficient to stabilize the composition refers to a quantity of non-surfactant electrolyte above the quantity that may exist in the composition, due to the presence of another ingredient.

Some embodiments provide a composition wherein the active compound is selected from magnolol, honokiol, tetrahydromagnolol, and tetrahydrohonokiol, and mixtures thereof. In some embodiments, the active compound is a derivative of magnolol, honokiol, tetrahydromagnolol, or tetrahydrohonokiol, such as those described in JP 2007-033649; WO 2006/071654; WO 2006/101818; and WO 2006/101864. In some embodiments, the derivative is a halogenated derivative.

In some embodiments, the active compound is present at a concentration of from about 0.01 to about 10% by weight of the composition. In other embodiments, the active compound is present at a concentration of from about 0.1 to about 7.5% by weight of the composition. In further embodiments, the active compound is present at a concentration of from about 0.25 to about 5% by weight of the composition. In some embodiments, the active compound is present at a concentration of from about 0.5 to about 2.5% by weight of the composition. In some embodiments, the active compound is present at a concentration of from about 1 to about 2% by weight of the composition. Still other embodiments provide compositions wherein the active compound is present at a concentration of about 1.3%, by weight of the composition.

In some embodiments, the non-surfactant electrolyte is selected from: sodium sulfate, sodium chloride, calcium chloride, potassium chloride, and a combination of two or more thereof. In some embodiments, the non-surfactant electrolyte is sodium sulfate. In some embodiments, the non-surfactant electrolyte is present at a concentration of from about 0.1 to about 10%, by weight of the composition. In other embodiments, the non-surfactant electrolyte is present at a concentration of from about 0.5 to about 7.5%, by weight of the composition. In other embodiments, the non-surfactant electrolyte is present at a concentration of from about 1 to about 5%, by weight of the composition. Yet other embodiments provide compositions wherein the non-surfactant electrolyte is present at a concentration of about 2% by weight of the composition.

In some embodiments, the composition is in a form selected from: a mouthrinse, toothpaste, a lozenge, a confectionary, and a dissolvable tablet.

In some embodiments, the composition further comprises one or more components selected from: a fluoride ion source, an abrasive, a surfactant, a foaming agent, a vitamin, a polymer, an enzyme, a humectant, a thickener, an antimicrobial agent, a preservative, a flavoring agent and a colorant. In some embodiments, at least one of the one or more components is a fluoride ion source selected from: stannous fluoride, sodium fluoride, potassium fluoride, sodium monofluorophosphate, sodium fluorosilicate, ammonium fluorosilicate, amine fluoride, ammonium fluoride, and a combination of two or more thereof.

Some embodiments provide a method of treating a disease or condition of the oral cavity comprising contacting an oral cavity surface with any one of the compositions described herein. In some embodiments, the disease or condition of the oral cavity is an inflammatory disease or condition. In some embodiments, the disease or condition of the oral cavity is selected from gingivitis, periodontitis and halitosis. In some embodiments, the compositions of the present invention can be used in a method to reduce, inhibit or prevent bacterial growth in the oral cavity. In some embodiments, the compositions can be used in a method to reduce bacterial count in the oral cavity. In some embodiments, the compositions can be used in a method to inhibit growth and/or formation of biofilm and/or plaque.

In some embodiments, the oral compositions of the present invention are bactericidal against representative oral bacteria, such as *S. mutans, F. nucleatum, V. parvula, A. naeslundii*, and *P. gingivitis*. In some embodiments, the compositions of the present invention are highly efficacious against both gram-positive and gram-negative bacteria.

Magnolia Extracts

The compositions of the present invention contain at least one active compound found in an extract of magnolia. As referred to here, such an "extract" of magnolia is an extract from dried cortex, or bark, of a plant from the Magnoliaceae family, such as *Magnolia officinalis*, (hereinafter "magnolia") or a synthetic or semi-synthetic equivalent of such an extract or an active component thereof. In certain embodiments, the antibacterial ingredient in the active composition comprises one or more active compounds that have been isolated from an extract of magnolia. In other embodiments, the antibacterial ingredient comprises an extract of magnolia. The terms magnolia extract (which includes the extract and at least one active compound) and one or more active compounds from an extract of magnolia are used interchangeably herein.

Preferably, extracts of Magnolia Cortex (the bark of *Magnolia officinalis*) contain active compounds including, for example: magnolol, honokiol, tetrahydromagnolol, and tetrahydrohonokiol, which have demonstrated bactericidal properties against representative oral bacteria *S. mutans, F. nucleatum, V. parvula, A. naeslundii, P. gingivitis*. It should be noted that any plant from the Magnoliaceae family is suitable for the present invention and may be used in alternate embodiments. In some embodiments, the extract comprises an antimicrobial or antibacterial effective concentration or amount of a compound selected from the group consisting of magnolol, honokiol, tetrahydromagnolol, tetrahydrohonokiol, and mixtures thereof.

In some embodiments, the extract of magnolia may be obtained from dried Magnolia plant bark and can be prepared by any means known or to be developed in the art.

In various embodiments, it is preferred that the magnolia extract contains magnolol, honokiol, or both, the structure of each are as follows:

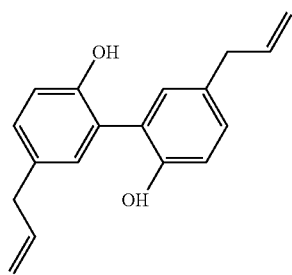

Magnolol

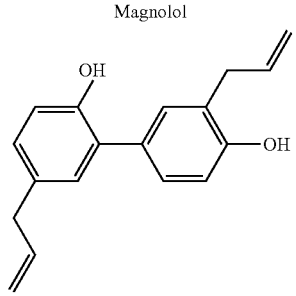

Honokiol

Additionally, tetrahydromagnolol and tetrahydrohonokiol, hydrogenated analogs of magnolol and honokiol, may be preferred or included in the composition as part of the extract.

In various embodiments, the magnolia extract comprises magnolol at a concentration of from about 2 to about 95%, by weight of the extract.

In various embodiments of the present invention, the oral care composition comprises a safe and effective amount of one or more active compounds from the magnolia extract.

One skilled in the art will appreciate that the concentration of the one or more active compounds (or the magnolia extract containing the active compounds) in the oral care composition will depend upon the relative concentration of the active compounds in the extract, and as such, it is contemplated that the amount of magnolia extract present may vary.

In various embodiments, additional antibacterial, antioxidant and/or anti-inflammatory active ingredients may be included in the oral care compositions. If added, the antibacterial active ingredients should not react with or detract from the efficacy and bioavailability of the one or more active compounds from magnolia extract.

Non-Surfactant Electrolytes

The inventors of the present invention have discovered that the presence of certain concentrations of a non-surfactant electrolyte can enhance the stability of the compositions described herein. The stability of the compositions may be determined by measuring, for example, the liquid clarity, and speed of phase separation. A stable liquid formulation will, for example, remain clear, and exhibit minimal to undetectable phase separation.

In some embodiments, the non-surfactant electrolyte increases the solubility of the magnolia extract component and/or enhances the stability of the formulation.

The non-surfactant electrolyte, when present, should be present in an amount which facilitates formation of the stable composition and/or solubility of the magnolia extract component. Generally, this amount is from about 0.001% by weight to about 10% by weight of the composition, or from about 0.01% to about 3% by weight of the composition, or less than about 2%, or about 2% by weight of the composition, but may be varied if required.

Oral Care Compositions

The vehicle or carrier in which the active compound from an extract of magnolia and non-surfactant electrolyte may be formulated may be any vehicle or mixture of vehicles which is suitable for oral or topical use; the type chosen will depend on the intended mode and site of application. Many such vehicles are known to those skilled in the art and are readily available commercially. Examples may for instance be found in "Oral Hygiene Products and Practice", 1988, Morton Prader, Ed., Marcel Dekker, Inc., New York, N.Y., USA. The active compound from an extract of magnolia and non-surfactant electrolyte may be present in the form of a suspension or other type of multi-phase dispersion.

Also as described above, the vehicle may be such as to target a desired site and/or time of delivery of the formulation. It may for instance target the formulation to the gums or teeth or other areas within the oral cavity; or it may delay or otherwise control release of the formulation over a particular time period. In some embodiments, the active compound from an extract of magnolia and the non-surfactant electrolyte may be microencapsulated, for instance in liposomes.

The formulation should contain an orally acceptable and systemically non-toxic vehicle or carrier. For example, where it takes the form of toothpaste, a typical vehicle might include water and a humectant to provide a liquid base, together with one or more of a thickener, a surfactant and a polishing agent. Suitable humectants include glycerol, sorbitol and polyethylene glycol, and particular mixtures thereof. A polyethylene glycol humectant may for example have a molecular weight range of from 200 to 1000 or from 400 to 800, such as about 600.

Suitable thickeners for use in toothpaste formulations include natural and synthetic gums and colloids such as carrageenan, xanthan gum and sodium carboxymethyl cellulose, as well as gum tragacanth; starch; polyvinyl pyrrolidone; cellulosic thickeners such as hydroxyethyl propyl cellulose, hydroxybutyl methyl cellulose, hydroxypropyl methyl cellulose, hydroxyethyl cellulose and water soluble salts of cellulose ethers such as sodium carboxymethyl cellulose or sodium carboxymethyl hydroxyethyl cellulose; and carboxyvinyl polymers. Suitable inorganic thickeners include colloidal silica, colloidal magnesium aluminium silicate, finely divided silica and synthetic hectorite. Mixtures of thickeners may also be used.

Suitable surfactants for use in toothpaste formulations prepared according to the invention include water soluble detergents. In general they may be anionic, nonionic, cationic, zwitterionic, amphoteric or ampholytic, but are preferably anionic.

Examples of suitable anionic surfactants include higher alkyl sulfates such as sodium lauryl sulfate, and higher fatty acid esters of 1,2 dihydroxy propane sulphonate. Examples of suitable water soluble nonionic surfactants include the polymeric condensation products of hydrophilic alkylene oxide group-containing compounds (typically ethylene oxide) with organic hydrophobic compounds (for example those having aliphatic chains of about 12 to 20 carbon atoms). Such products include the "ethoxamers" and include for example the condensation products of poly(ethylene oxide) with fatty acids, fatty alcohols, fatty amides and other fatty moieties, as well as with propylene oxide and polypropylene oxides (the latter being available, for example, under the trade name Pluronic®).

In some embodiments, the compositions contain an abrasive or polishing agent. Suitable such agents include siliceous materials (including gels and precipitates, such as precipitated amorphous hydrated silicas, aluminium silicate, zirconlure silicate, silica gel and colloidal silica); carbonates and bicarbonates such as calcium carbonate and sodium bicarbonate; phosphates such as sodium metaphosphate, potassium metaphosphate, tricalcium phosphate, dicalcium orthophosphate dehydrate, calcium phosphate dihydrate, anhydrous dicalcium phosphate, calcium pyrophosphate, calcium polymetaphosphate, magnesium orthophosphate, trimagnesium phosphate and insoluble sodium polymetaphosphate; alumina trihydrate; calcined alumina; bentonite; complex amorphous alkali metal aluminosilicates; and resinous abrasive materials such as particulate condensation products of urea and formaldehyde. Mixtures of such polishing agents may also be used. The abrasive or polishing agent should not excessively abrade tooth enamel or dentin. Silica abrasive agents may be particularly preferred for use in the present invention. Abrasives may be used in amounts up to about 75% w/w of the composition, preferably in amounts from about 5% w/w to about 40% w/w of the composition, and most preferably from about 5% w/w to about 30% w/w of the composition.

Where a formulation prepared according to the invention takes the form of a mouthwash or other aqueous composition, it may for example contain a water/alcohol (e.g., water/ethyl alcohol) solution and optionally one or more other ingredients selected for example from flavoring agents, sweeteners, humectants, surfactants, emulsifiers, and mixtures thereof. Suitable humectants include those described above, in particular glycerol and sorbitol. One or more additional antibacterial agents may also be included.

Non-soap surfactants (for example nonionic, cationic or amphoteric surfactants) may be preferred for use in mouthwash formulations. Suitable nonionic surfactants include the condensation products of hydrophilic alkylene oxide group-containing compounds with organic hydrophobic compounds, as described above. Other suitable nonionic synthetic detergents include: the polyethylene oxide condensates of alkyl phenols; those derived from the condensation of ethylene oxide with the product resulting from the reaction of propylene oxide and ethylene diamine; the condensation products of aliphatic alcohols having from 8 to 18 carbon atoms with ethylene oxide; and the polyoxyethylene derivatives of fatty acid partial esters of sorbitol anhydride (for example the commercially available Tween® products).

Suitable cationic detergents include quaternary ammonium compounds, in particular those having one long alkyl chain of about 8 to 18 carbon atoms, for example lauryl trimethylammonium chloride, cetyl pyridinium chloride, cetyl trimethylammonium bromide, di-isobutylphenoxyethyldimethylbenzylammonium chloride, coconutalkyltrimethylammonium nitrite, cetyl pyridinium fluoride and the like.

Suitable amphoteric detergents include derivatives of aliphatic secondary and tertiary amines in which one of the aliphatic substituents contains from about 8 to 18 carbon atoms and one contains an anionic water solubilizing group such as carboxylate, sulphate, sulphonate, phosphate or phosphonate.

Other suitable surfactants, for use in formulations according to the invention, may be found in McCutcheon's Detergents and Emulsifiers.

A formulation prepared according to the invention may contain one or more components selected from abrasives, bleaching agents, tooth whitening agents (e.g., peroxides or sodium perborate), surface active agents/detergents as described above, foaming agents, a fluoride ion source, zinc salts, non-cariogenic sweeteners such as saccharin or aspartame or dextrose or levulose, other flavoring agents such as peppermint or spearmint or aniseed, menthol, desensitizing agents, anti-tartar/sequestering agents or anti-calculus agents (for example metal salts such as zinc chloride, zinc acetate or zinc oxide; pyrophosphate salts such as alkali metal or ammonium pyrophosphates; or diphosphonates), sodium bicarbonate, anionic polycarboxylates, enzymes such as lactoperoxidases, humectants as described above, binders such as carboxyvinyl polymers, pH regulating buffers, preservatives, colors/dyes (for example chlorophyll or titanium dioxide), plant extracts, anti-plaque agents, additional antimicrobial (for example antifungal or antibacterial, especially antibacterial) agents and mixtures thereof.

In some embodiments, the additional antimicrobial agent is selected from the group consisting of biocides, disinfectants, antiseptics, antibiotics, bacteriophages, enzymes, anti-adhesins, immunoglobulins and mixtures thereof; it is preferably active as a bactericide, in particular against *P. gingivalis* and/or against one or more other bacteria implicated in oral health problems.

Where the oral composition of the present invention is a gel or paste such as in toothpaste, an orally acceptable carrier, including a water-phase with humectant which is preferably glycerin or sorbitol or an alkylene glycol such as polyethylene glycol or propylene glycol, may be present. Such gel or paste compositions typically further contain a natural or synthetic thickener or gelling agent.

The mouthwash form of the oral composition may be suitably prepared by mixing the appropriate components thereof.

The oral compositions of the present invention may be incorporated into solids such as lozenges, or in chewing gum or other products, e.g. by stirring into a warm gum base or coating the outer surface of a gum base, illustrative of which may be mentioned jelutone, rubber latex, vinylite resins, and the like, desirably with conventional plasticizers or softeners, sugar or other sweeteners or carbohydrates such as glucose, sorbitol and the like.

The orally acceptable carrier for a tablet or lozenge is desirably a non-cariogenic solid water-soluble polyhydric alcohol (polyol) such as mannitol, xylitol, sorbitol, maltitol, a hydrogenated starch hydrolysate, Lycasin®, hydrogenated glucose, hydrogenated disaccharides or hydrogenated polysaccharides.

In some embodiments, the fluoride ion source is present in an amount by weight of up to about 1.2% w/w, preferably from about 0.1% w/w to about 1.0% w/w, and most preferably from about 0.175% w/w to about 0.8% w/w, of the dentifrice composition so as to release 800-1500 ppm F-.

Sweeteners well known in the art, including natural and artificial sweeteners, may be used. The sweetener may be selected from a wide range of materials including naturally occurring water-soluble sweeteners, artificial water-soluble sweeteners and modified water-soluble sweeteners derived from naturally occurring water-soluble sweeteners.

Flavoring agents which may be used in the invention include natural and artificial flavors known in the dentifrice art. Suitable flavoring agents include, but are not limited to, mints, such as peppermint, citrus flavors such as orange and lemon, artificial vanilla, cinnamon, various fruit flavors, and the like. Anethole (or anise camphor, p-propenyl anisole) is a flavor constituent of anise and fennel oils which are used widely as flavoring agents and antiseptics and was found useful in masking the harsh taste of thymol.

Colorants may also be used, and when used, may be incorporated in amounts up to about 3%, by weight. The colorants may also include natural food colors and dyes suitable for food, drug and cosmetic applications.

Suitable preservatives in this invention include benzoic acid, butylated hydroxyanisole (BHA), butylated hydroxytoluene (BHT), ascorbic acid, methyl paraben, propyl paraben, tocopherol, and mixtures thereof. When used, preservatives are generally present in amounts up to about 1% w/w.

Embodiments of the present invention are further described in the following examples. The examples are merely illustrative and do not in any way limit the scope of the invention as described and claimed.

EXAMPLES

Example 1

A flavor premix (Part 1) can be made by adding a quantity of flavoring agent and PEG 400 to a quantity of honokiol. This is mixed until the honokiol is fully solubilized. A quantity of sodium lauryl sulfate is then added, and mixed.

An aqueous phase (Part 2) can be prepared by adding a quantity of saccharin, sodium fluoride and sodium sulfate to water. This is mixed until all the solids are substantially dissolved. Glycerin and sorbitol are then added, and mixed until homogenized.

The aqueous phase (Part 2) is added to the flavor premix (Part 1), and mixed until a homogeneous solution is obtained.

Example 2

Product stability can be evaluated using an optical centrifugation method and by visual observation of phase separation. In optical centrifugation, the physical stability is monitored by centrifuging the samples at 500 rpm for 2 hrs and recording phase separation using optical sensors. This method accelerates the ageing process, and the results can be used to predict the long-term stability of a composition.

Example 3

Several compositions were prepared by the process described in Example 1. Table 1 (below) describes the formulations of two exemplary compositions of the present invention (Compositions I and II) and two comparative compositions which do not contain an effective amount of non-surfactant electrolyte (Compositions X and Y).

TABLE 1

| Ingredient | Composition | | | |
| --- | --- | --- | --- | --- |
| | I | II | X | Y |
| | % w/w | | | |
| Sodium sulfate | 2 | 2 | — | — |
| PEG 400 | 2.8 | 2.8 | 2.8 | 2.8 |
| Gantrez (13% solution) | 41 | 41 | 41 | 41 |
| Sodium hydroxide (50% solution) | 3.3 | 3.3 | 3.3 | 3.3 |
| Flavor | 1.3 | 1.3 | 1.3 | 1.3 |
| Honokiol | 1.3 | 1.3 | 1.3 | 1.3 |
| Sodium lauryl sulfate | 2.1 | 2.7 | 2.1 | 2.7 |
| Sodium saccharin | 0.2 | 0.2 | 0.2 | 0.2 |
| Sodium fluoride | 0.1 | 0.1 | 0.2 | 0.1 |
| Sorbitol | 11.9 | 11.2 | 12.5 | 11.8 |
| Glycerin | 11.8 | 11.1 | 12.3 | 11.7 |
| Water | q.s. | q.s. | q.s. | q.s |

Physical stability of the compositions was measured on a scale of 1 to 10; wherein stability is measured in terms of clarity and phase separation. A score of "10" indicates that the phases remain substantially unseparated; while a score of "1" indicates that an unacceptable level of phase separation has occurred. Phase separation can be used to identify a product having unacceptable long-term stability.

Compositions I and II, having physical stability scores of 7 and 6.5, respectively, demonstrated minimal phase separation; while complete phase separation was observed in Compositions X and Y, which had physical stability scores of 5 and 2.8, respectively. These results demonstrate that the addition of an effective amount of a non-surfactant electrolyte to a formulation comprising an active compound from an extract of magnolia, as described herein, provides a composition with acceptable long-term stability; whereas similarly formulated compositions lacking an effective amount of a non-surfactant electrolyte as described herein, do not have acceptable long-term stability.

TABLE 2

| Composition | Physical Stability Score |
| --- | --- |
| I | 7 |
| II | 6.5 |
| X | 5 |
| Y | 2.8 |

As those skilled in the art will appreciate, numerous changes and modifications may be made to the embodiments described herein without departing from the spirit of the invention. It is intended that all such variations fall within the scope of the appended claims.

What is claimed is:

1. An oral care composition comprising:
   a liquid comprising a mixture of:
   an antibacterial effective amount of an active compound from an extract of magnolia;
   sodium sulfate at a concentration of about 2% by weight of the composition;
   at least one fluoride ion source selected from: stannous fluoride, sodium fluoride, potassium fluoride, sodium monofluorophosphate, sodium fluorosilicate, ammonium fluorosilicate, amine fluoride, ammonium fluoride, and a combination of two or more thereof; and
   an orally acceptable carrier,
   wherein said liquid does not exhibit complete phase separation upon centrifuging at 500 rpm for 2 hours;
   wherein the active compound is selected from honokiol, tetrahydromagnolol, and tetrahydrohonokiol, and mixtures thereof; and wherein the active compound is present at a concentration of about 1 to about 2% by weight of the composition.

2. The composition according to claim 1, wherein the active compound is honokiol.

3. The composition according to claim 1, wherein the active compound is present at a concentration of about 1 to about 1.5% by weight of the composition.

4. The composition according to claim 1, wherein the active compound is present at a concentration of about 1.3%, by weight of the composition.

5. The composition according to claim 1, wherein the composition is in a form selected from: a mouthrinse, toothpaste, a lozenge, a confectionary, and a dissolvable tablet.

6. The composition according to claim 1, further comprising one or more components selected from: an abrasive, a surfactant, a foaming agent, a vitamin, a polymer, an enzyme, a humectant, a thickener, an antibacterial agent, a preservative, a flavoring agent and a colorant.

7. A method of treating a disease or condition of the oral cavity comprising contacting an oral cavity surface with a composition of claim 1.

8. The method of claim 7, wherein the disease or condition of the oral cavity is selected from gingivitis, periodontitis and halitosis.

* * * * *